United States Patent [19]
Macor et al.

[11] Patent Number: 5,594,014
[45] Date of Patent: Jan. 14, 1997

[54] INDOLE DERIVATIVES AS 5-HT1 AGONISTS

[75] Inventors: John E. Macor, Salem; Jolanta T. Nowakowski, Haddam, both of Conn.

[73] Assignee: Pfizer Inc, New York, N.Y.

[21] Appl. No.: 284,662

[22] PCT Filed: Mar. 3, 1993

[86] PCT No.: PCT/US93/01667

§ 371 Date: Aug. 19, 1994

§ 102(e) Date: Aug. 19, 1994

[87] PCT Pub. No.: WO93/18032

PCT Pub. Date: Sep. 16, 1993

[51] Int. Cl.$^6$ .............. C07D 417/14; C07D 413/14; A61K 31/40
[52] U.S. Cl. .............. 514/364; 514/365; 548/131; 548/181
[58] Field of Search .............. 548/181, 131; 514/364, 365

[56] References Cited

U.S. PATENT DOCUMENTS

| | | | |
|---|---|---|---|
| 4,252,803 | 2/1981 | Webb | 424/248.5 |
| 4,839,377 | 6/1989 | Bays et al. | 514/415 |
| 4,855,314 | 8/1989 | Oxford ert al. | 514/415 |
| 5,208,248 | 5/1993 | Baker et al. | 514/364 |
| 5,298,491 | 3/1994 | Chauveau | 514/17 |

FOREIGN PATENT DOCUMENTS

| | | |
|---|---|---|
| 0303506 | 8/1988 | European Pat. Off. |
| 0313397 | 10/1988 | European Pat. Off. |
| 0354777 | 8/1989 | European Pat. Off. |
| 0438230 | 7/1991 | European Pat. Off. |
| 0497512 | 8/1992 | European Pat. Off. |
| 9118897 | 12/1991 | WIPO |

OTHER PUBLICATIONS

W. Feniuk, et al., P. P. A. Humphrey & M. J. Perren—Br. J. Pharmacol. (1989), 96, 83–90.
P. P. A. Humphrey, et al.,—Br. J. Pharmacol. (1988), 94, 1123–1132.
D. Hoyer, et al., *Eur. J. Pharm.*, 118, 13 (1985).
R. E. Hearing, et al. *J. Neuroscience*, 7, 894 (1987).
P. Sauerberg, et al. *J. Med. Chem.*, 34, 682 (1991).
G. A. Showell, et al., *J. Med. Chem.*, 34, 1086 (1991).

*Primary Examiner*—Robert Gerstl
*Attorney, Agent, or Firm*—Peter C. Richardson; Paul H. Ginsburg; Grover F. Fuller, Jr.

[57] ABSTRACT

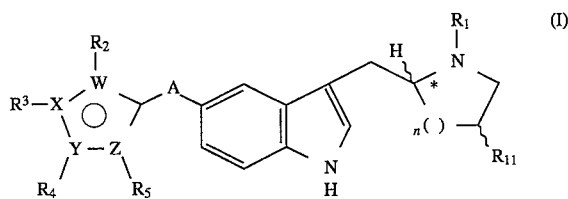

Compounds of the formula (I) where A represents a direct bond, $C_1$–$C_4$ alkyl, or $C_1$–$C_4$ alkenyl; n is 0, 1, or 2; W, X, Y, and Z are each independently oxygen, sulfur, nitrogen or carbon, provided that at least one of W, X, Y, or Z is nitrogen. These compounds are useful psychotherapeutics and are potent serotonin (5-HT$_1$) agonists and may be used in the treatment of depression, anxiety, eating disorders, obesity, drug abuse, cluster headache, migraine, pain and chronic paroxysmal hemicrania and headache associated with vascular disorders, and other disorders arising from deficient serotonergic neurotransmission. The compounds can also be used as centrally acting antihypertensives and vasodilators.

17 Claims, No Drawings

INDOLE DERIVATIVES AS 5-HT1 AGONISTS

This application is a 371 of PCT/US93/01667 filed Mar. 3, 1993.

BACKGROUND OF THE INVENTION

The present invention relates to indole derivatives, to processes and intermediates for their preparation, to pharmaceutical compositions containing them and to their medicinal use. The active compounds of the present invention are useful in treating migraine and other disorders.

U.S. Pat. Nos. 4,839,377 and 4,855,314 and European Patent Application Publication Number 313397 refer to 5-substituted 3-aminoalkyl indoles. The compounds are said to be useful for the treatment of migraine.

British Patent Application 040279 refers to 3-aminoalkyl-1H-indole-5-thioamides and carboxamides. The compounds are said to be useful in treating hypertension, Raymond's disease and migraine.

European Patent Application Publication Number 303506 refers to 3-poly:hydropyridyl-5-substituted-1H-indoles. The compounds are said to have 5-HT$_1$ receptor agonist and vasoconstrictor activity and to be useful in treating migraine.

European Patent Application Publication Number 35477 refers to N-piperidinyl:indolyl:ethyl-alkane sulfonamide derivatives. The compounds are said to have 5-HT$_1$ receptor agonist and vasoconstrictor activity and to be useful in treating cephalic pain.

European Patent Application Publication Numbers 438230, 494774, and 497512 refer to indole-substituted five-membered heteroaromatic compounds. The compounds are said to have 5-HT$_1$-like receptor agonist activity and to be useful in the treatment of migraine and other disorders for which a selective agonist of these receptors is indicated.

SUMMARY OF THE INVENTION

The present invention relates to compounds of the formula

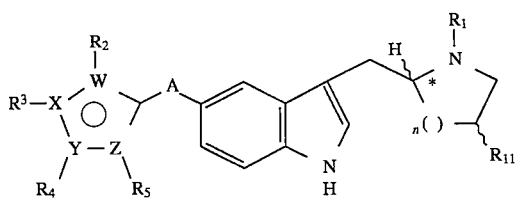

where A represents a direct bond, $C_1$–$C_4$ alkyl, or $C_1$–$C_4$ alkenyl; n is 0, 1, or 2; $R_1$ is hydrogen, $C_1$–$C_6$ alkyl, aryl, $C_1$–$C_3$ alkylaryl, $C_1$–$C_3$ alkylheteroaryl, or —$(CH_2)_m R_6$; W, X, Y, and Z are each independently oxygen, sulfur, nitrogen or carbon, provided that at least one of W, X, Y, or Z is nitrogen; $R_2$, $R_3$, $R_4$, and $R_5$ are each independently hydrogen, $C_1$–$C_6$ alkyl, aryl, $C_1$–$C_3$ alkylaryl, $C_1$–$C_3$ alkylheteroaryl, halogen, cyano, trifluoromethyl, nitro, —$OR_7$, —$NR_7R_8$, —$(CH_2)_s OR_7$, —$SR_7$, —$SO_2NR_7R_8$, —$NR_7SO_2R_8$, —$NR_7CO_2R_8$, —$CONR_7R_8$, or —$CO_2R_7$; one of $R_2$ and $R_3$, $R_3$ and $R_4$, or $R_4$ and $R_5$ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O or S; $R_6$ is cyano, trifluoromethyl, or —$OR_9$; $R_7$, $R_8$, and $R_9$ are each independently hydrogen, $C_1$ to $C_6$ alkyl, —$(CH_2)_m R_{10}$, $C_1$ to $C_3$ alkylaryl, or aryl; $R_7$ and $R_8$ may be taken together to form a $C_4$–$C_7$ alkyl ring; $R_{10}$ is cyano, trifluoromethyl, or $C_1$–$C_4$ alkoxy; $R_{11}$ is hydrogen, —$OR_{12}$, or —$NHCOR_{12}$; $R_{12}$ is $C_1$ to $C_6$ alkyl, aryl, or $C_1$ to $C_3$ alkyl-aryl; m is 1, 2, or 3; s is 0, 1, 2, or 3; and the above aryl groups and the aryl moieties of the above alkylaryl groups are independently selected from phenyl and substituted phenyl, wherein said substituted phenyl may be substituted with one to three groups selected from $C_1$ to $C_4$ alkyl, halogen (e.g. fluorine, chlorine, bromine or iodine), hydroxy, cyano, carboxamido, nitro, and $C_1$ to $C_4$ alkoxy, and the pharmaceutically acceptable salts thereof. These compounds are useful in treating migraine and other disorders.

The compounds of the invention include all optical isomers of formula I (e.g., R and S stereogenicity at any chiral site) and their racemic, diastereomeric, or epimeric mixtures. When $R_{11}$ is hydrogen, the epimers with the R absolute configuration at the chiral carbon site designated by an asterisk in formula I are preferred. When $R_{11}$ is —$OR_{12}$ or —$NHCOR_{12}$ and n is 0 or 1, the epimers with the S absolute configuration at the chiral carbon site designated by an asterisk in formula I are preferred. When $R_{11}$ is —$OR_{12}$ or —$NHCOR_{12}$ and n is 2, the epimers with the R absolute configuration at the chiral carbon site designated by an asterisk in formula I are preferred. When $R_{11}$ is —$OR_{12}$ or —$NHCOR_{12}$ and n is 0, the cis epimers [(2S, 3S) absolute configuration in the azetidine ring] are particularly preferred. When $R_{11}$ is —$OR_{12}$ or —$NHCOR_{12}$ and n is 1, the cis epimers [(2S, 4R) absolute configuration in the pyrrolidine ring] are particularly preferred. When $R_{11}$ is —$OR_{12}$ or —$NHCOR_{12}$ and n is 2, the cis epimers [(2R, 5R) absolute configuration in the piperidine ring] are particularly preferred.

Unless otherwise indicated, the alkyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

Preferred compounds of the invention are compounds of the formula I wherein A is either a direct bond or —$CH_2$—; n is 1; $R_1$ is hydrogen, $C_1$–$C_4$ alkyl or —$CH_2CH_2OCH_3$; Z is nitrogen; Y is carbon; W and X are each independently oxygen, sulfur, nitrogen or carbon; and $R_2$, $R_3$, and $R_4$ are as defined above. Of the foregoing preferred compounds, when $R_{11}$ is hydrogen, the epimers with the R absolute configuration at the chiral carbon site designated by an asterisk in formula I are more preferred. Of the foregoing preferred compounds, when $R_{11}$ is —$OR_{12}$ or —$NHCOR_{12}$, the epimers with the S absolute configuration at the chiral carbon site designated by an asterisk in formula I are more preferred. Of the foregoing compounds, when $R_{11}$ is —$OR_{12}$ or —$NHCOR_{12}$, the cis epimers [(2S, 4R) absolute configuration in the pyrrolidine ring] are particularly preferred.

The following compounds are particularly preferred:

(R)-5-(4-benzyl-1,3-thiazol-2-yl)-3-(N-methylpyrrolidin-2-ylmethyl)-1 H-indole;

(R)-5-(4-benzyl-1,3-thiazol-2-yl)-3-(pyrrolidin-2-ylmethyl)-1H-indole;

(R)-5-(3-benzyl-1,2,4-oxadiazol-5yl)-3-(N-methylpyrrolidin-2-ylmethyl)-1H-indole;

(R)-5-(3-benzyl-1,2,4-oxadiazol-5-yl)-3-(pyrrolidin-2-ylmethyl)-1H-indole;

(R)-5-(3-benzyl-1,2,4-oxadiazol-5-ylmethyl)-3-(N-methylpyrrolidin-2-ylmethyl)-1H-indole; and (R)-5-(3-benzyl-1,2,4-oxadiazol-5-ylmethyl)-3-(pyrrolidin-2-ylmethyl)-1H-indole.

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of a compound of the formula I or a pharmaceutically acceptable salt thereof effective in treating such condition.

The present invention also relates to a pharmaceutical composition for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a compound of the formula

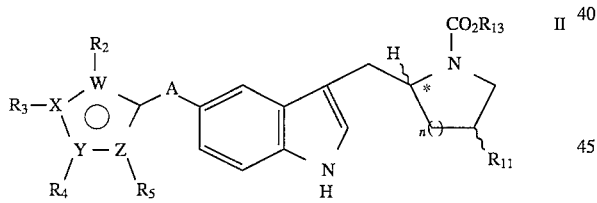

where $n$, $A$, $W$, $X$, $Y$, $Z$, $R_2$, $R_3$, $R_4$, $R_5$, and $R_{11}$ are as defined above; and $R_{13}$ is $C_1$–$C_6$ alkyl, aryl, or alkylaryl (preferably benzyl). When $R_{11}$ is hydrogen, the epimers with the R absolute configuration at the chiral carbon site designated by an asterisk in formula II are preferred. When $R_{11}$ is —$OR_{12}$ or —$NHCOR_{12}$ and n is 0 or 1, the epimers with the S absolute configuration at the chiral carbon site designated by an asterisk in formula II are preferred. When $R_{11}$ is —$OR_{12}$ or —$NHCOR_{12}$ and n is 2, the epimers with the R absolute configuration at the chiral carbon site designated by an asterisk in formula II are preferred. When $R_{11}$ is —$OR_{12}$ or —$NHCOR_{12}$ and n is 0, the cis epimers [(2S, 3S) absolute configuration in the azetidine ring] are particularly preferred. When $R_{11}$ is —$OR_{12}$ or —$NHCOR_{12}$ and n is 1, the cis epimers [(2S, 4R) absolute configuration in the pyrrolidine ring] are particularly preferred. When $R_{11}$ is —$OR_{12}$ or —$NHCOR_{12}$ and n is 2, the cis epimers [(2R, 5R) absolute configuration in the piperidine ring] are particularly preferred. The compounds of formula II are useful as intermediates in preparing compounds of formula I.

The present invention also relates to a compound of the formula

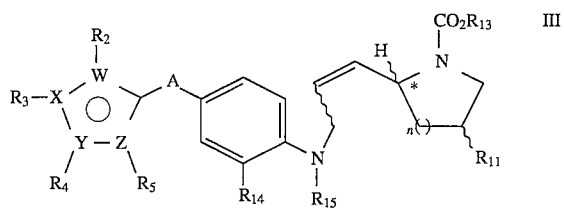

where $n$, $A$, $W$, $X$, $Y$, $Z$, $R_2$, $R_3$, $R_4$, $R_5$, $R_{11}$ and $R_{13}$ are as defined above; $R_{14}$ is halogen (e.g. fluorine, chlorine, bromine, or iodine [preferably bromine or iodine]); and $R_{15}$ is —$COCF_3$, —$SO_2CH_3$, —$SO_2Ph$ [Ph=phenyl], or —$CO_2C(CH_3)_3$ [preferably —$COCF_3$]. When $R_{11}$ is hydrogen, the epimers with the R absolute configuration at the chiral carbon site designated by an asterisk in formula III are preferred. When $R_{11}$ is —$OR_{12}$ or —$NHCOR_{12}$ and n is 0 or 1, the epimers with the S absolute configuration at the chiral carbon site designated by an asterisk in formula III are preferred. When $R_{11}$ is —$OR_{12}$ or —$NHCOR_{12}$ and n is 2, the epimers with the R absolute configuration at the chiral carbon site designated by an asterisk in formula III are preferred. When $R_{11}$ is —$OR_{12}$ or —$NHCOR_{12}$ and n is 0, the cis epimers [(2S, 3S) absolute configuration in the azetidine ring] are particularly preferred. When $R_{11}$ is —$OR_{12}$ or —$NHCOR_{12}$ and n is 1, the cis epimers [(2S, 4R) absolute configuration in the pyrrolidine ring] are particularly preferred. When $R_{11}$ is —$OR_{12}$ or —$NHCOR_{12}$ and n is 2, the cis epimers [(2R, 5R) absolute configuration in the piperidine ring] are particularly preferred. The compounds of formula III are useful as intermediates in preparing compounds of formula II.

DETAILED DESCRIPTION OF THE INVENTION

The compounds of the present invention are prepared via the following reaction scheme.

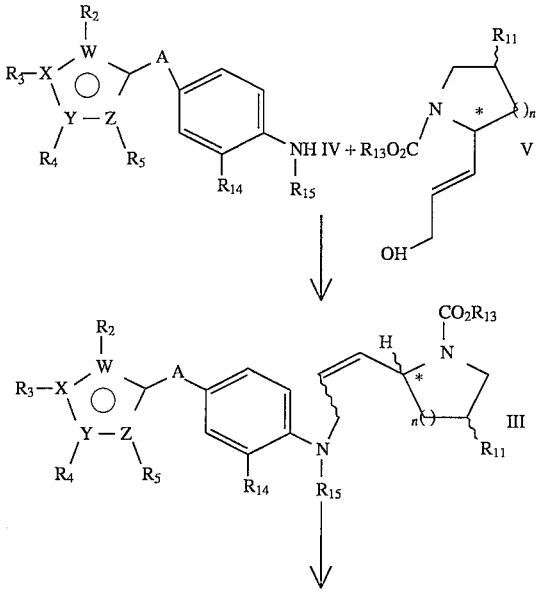

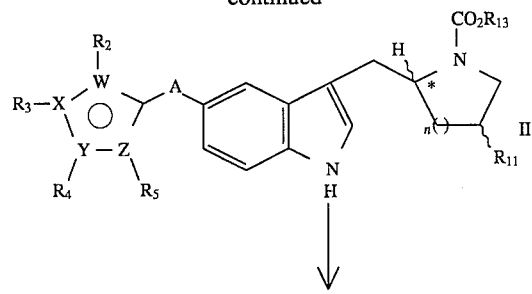

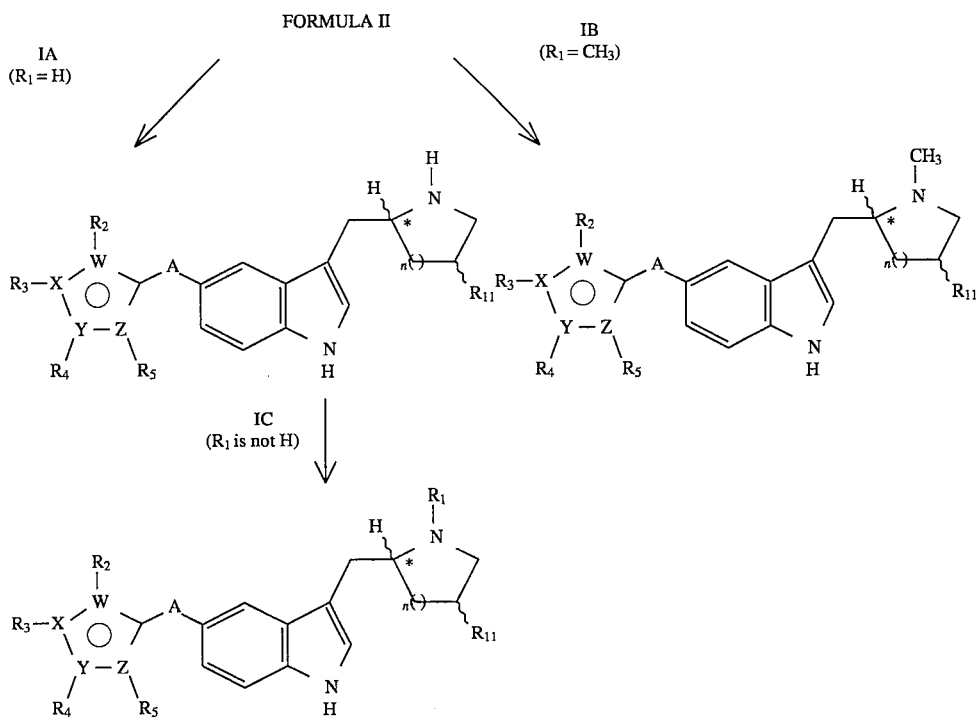

include N,N-dimethylformamide, acetonitrile, and N-methylpyrrolidine. The preferred solvent is N,N-dimethylformamide. Suitable phase transfer catalysts include tetraalkylammonium halides, and tetra-n-butylammonium chloride preferably the latter. Suitable bases include tertiary amines, sodium hydrogen carbonate, and sodium carbonate. The preferred base is triethylamine. The reaction is conducted at a temperature of from about 60° C. to about 180° C., preferably from about 80° C. to 100° C.

Compounds of formula IB ($R_1$=—$CH_3$) are prepared by hydride reduction of a compound of the formula II where n, A, W, X, Y, Z, $R_2$, $R_3$, $R_4$ and $R_5$ are as defined above, and $R_{13}$ is selected from $C_1$–$C_6$ alkyl, aryl, and alkylaryl (pref- Compounds of formula III can be prepared by the Mitsunobu coupling reaction of compounds of formulas IV and V wherein n, A, W, X, Y, Z, $R_2$, $R_3$, $R_4$, $R_5$, $R_{11}$, $R_{12}$, $R_{13}$, $R_{14}$, and $R_{15}$ are as defined above using a phosphine and an azodicarboxylate in a suitable solvent. Suitable phosphines include trialkyl phosphines and triarylphosphines, preferably triphenylphosphine. Suitable azodicarboxylates include dialkyl azodicarboxylates, preferably diethyl diazodicarboxylate. Suitable solvents include methylene chloride, ethers, (tetrahydrofuran, diethyl ether, and 1,4-dioxane), N,N-dimethylformamide and acetonitrile. The preferred solvent is tetrahydrofuran. The reaction is conducted at a temperature of from about 0° C. to about 65° C., most preferably at about 25° C.

Compounds of formula II can be prepared by the transition metal catalyzed cyclization of compounds of the formula III where n, A, W, X, Y, Z, $R_2$, $R_3$, $R_4$, $R_5$, $R_{11}$, and $R_{13}$ are as defined above, $R_{14}$ is halogen (preferably bromine or iodine) and $R_{15}$ is —$COCF_3$, —$SO_2CH_3$, —$SO_2Ph$, or —$CO_2C(CH_3)_3$, preferably trifluoromethylacetyl [—$COCF_3$], in a suitable inert solvent with a phase transfer catalyst and a base. Suitable catalysts include palladium salts such as palladium (II) acetate or palladium (II) chloride (preferably palladium acetate) and rhodium salts, such as tris(triphenyl)rhodium (I) chloride. Suitable solvents erably benzyl) with a hydride reducing agent in an inert solvent. Suitable hydride reducing agents include lithium aluminum hydride, diborane, lithium borohydride, and sodium amide. The preferred reagent is lithium aluminum hydride. Suitable solvents include ethers, such as diethyl ether, tetrahydrofuran, 1,4-dioxane and 1,2-dimethoxyethane. The preferred solvent is tetrahydrofuran. The reduction is conducted at a temperature of from about 30° C. to about 100° C., preferably from about 65° C. to about 70° C.

Compounds of formula IA ($R_1$=H) are prepared by catalytic reduction of a compound of the formula II where n, A, W, X, Y, Z, $R_2$, $R_3$, $R_4$, $R_5$ and $R_{13}$ are as defined above under an atmosphere of hydrogen, preferably at a pressure of about 1 to about 3 atmospheres, or using a hydrogen source such as ammonium formate or formic acid in an inert solvent. Suitable catalysts include palladium on carbon, Raney nickel, and platinum oxide. The preferred catalyst is palladium on carbon. Suitable solvents include $C_1$ to $C_6$ alcohols, N,N-dimethylformamide, ethyl acetate, and acetonitrile. The preferred solvent is ethanol. The reaction is conducted at a temperature of from about 0° C. to about 60° C., preferably about 25° C.

Compounds of formula IC ($R_1 \neq H$) are also prepared by the alkylation of a compound of the formula IA ($R_1$=H)

wherein $R_2$, $R_3$, $R_4$, $R_5$, $R_{11}$, W, X, Y, Z, A, and n are as defined above with an alkylating agent of the formula $R_1$-LG and a base in an inert solvent, where LG is a suitable leaving group and $R_1$ is as defined above except for hydrogen. Examples of suitable leaving groups include —I, —Br, —Cl, —OSO$_2$Ph, —OSO$_2$CH$_3$, and —OSO$_2$CF$_3$. Suitable alkylating agents include alkyl halides (chlorides, bromides, or iodides), alkyl tosylates, alkyl mesylates, alkyl triflates, α,β-unsaturated ketones, α,β-unsaturated esters, α,β-unsaturated amides, and α,β-unsaturated nitriles. Alkyl halides (iodides) are preferred. Suitable solvents include methylene chloride, chloroform, carbon tetrachloride, acetonitrile, tetrahydrofuran, diethyl ether, dioxane, N,N-dimethylformamide, ethanol, propanol, and methanol. The preferred solvent is acetonitrile. The reaction is conducted between a temperature of about 0° C. to about 150° C., preferable about 25° C. to about 65° C.

Compounds of formula V are prepared via the following reaction scheme.

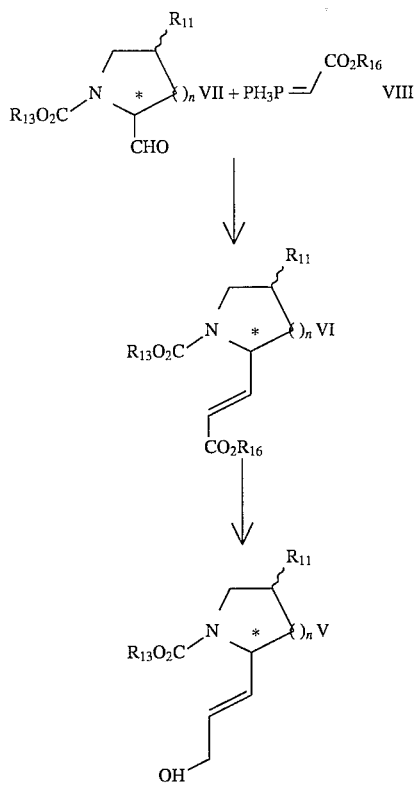

Compounds of the formula VI can be prepared using the Wittig reaction in a suitable solvent involving compounds of the formulas VII and VIII wherein n and $R_{13}$ are defined as above. $R_{16}$ is $C_1$–$C_6$ alkyl, aryl, or alkylaryl. Suitable solvents include ethers such a diethyl ether, tetrahydrofuran, and 1,4-dioxane. Tetrahydrofuran is the preferred solvent. The reaction is conducted at a temperature of from about −78° C. to about 30° C., preferably at about −78° C.

Compounds of the formula V can be prepared from a hydride reduction of a compound of formula VI wherein n, $R_{13}$ and $R_{16}$ are as defined above with a hydride reducing agent in an inert solvent. Suitable hydride reducing agents include lithium aluminum hydride, lithium borohydride, sodium borohydride, and diisobutylaluminum hydride. The preferred reagent is diisobutylaluminum hydride. Suitable solvents include ethers, such as diethyl ether, tetrahydrofuran, 1,4-dioxane and 1,2-dimethoxyethane. The preferred solvent is tetrahydrofuran. The reduction is conducted at a temperature of from about −100° C. to about 0° C., preferably from about −80° C. to about −70° C.

Compounds of the formula VII can be prepared using methods known to one skilled in the art, such as, for example, as outlined in S. Kiyooka, et al., *J. Org. Chem.*, 5409 (1989) and Y. Hamada, et al., *Chem. Pharm. Bull.*, 1921 (1982).

Compounds of the formula VIII are either commercially available or can be prepared using methods known to one skilled in the art, such as, for example, as outlined in L. Fieser and M. Fieser, *Reagents for Organic Synthesis*, John Wiley and Sons, New York, Vol. 1, p. 112 (1967).

Compounds of formula IV are prepared using the following reaction scheme.

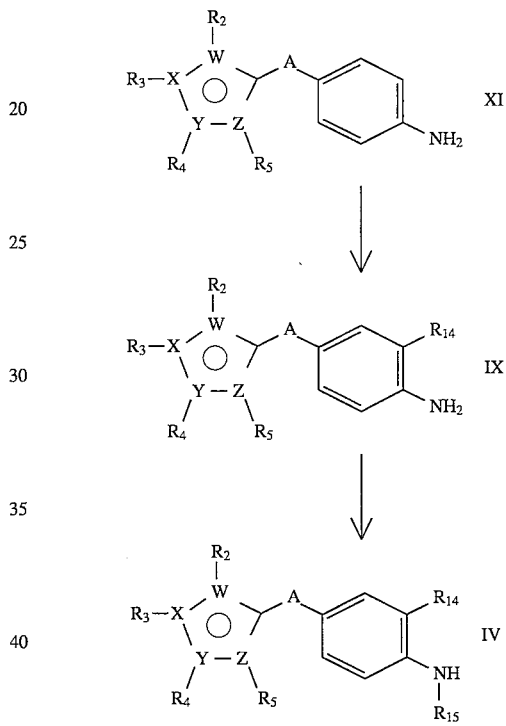

Compounds of formula IX can be prepared by reacting a compound of formula XI wherein A, W, X, Y, Z, $R_2$, $R_3$, $R_4$ and $R_5$ are as defined above with either chlorine, bromine, or iodine in a suitable solvent with a suitable base. Reaction with bromine is preferred. Suitable solvents include $C_1$–$C_6$ alcohols, methylene chloride, chloroform, or carbon tetrachloride. The preferred solvent is methanol. Suitable bases include triethylamine, pyridine, sodium carbonate, and sodium hydrogen carbonate. The preferred base is sodium hydrogen carbonate. The reaction is conducted at a temperature of from about 0° C. to about 65° C., preferably at about 25° C.

Compounds of formula IV can be prepared by reacting a compound of formula IX wherein A, W, X, Y, Z, $R_2$, $R_3$, $R_4$, $R_5$, and $R_{14}$ are as defined above with the acid chloride or symmetrical anhydride of the formula $R_{15}CO_2H$ in a suitable solvent with an suitable base. The preferred acid chloride or anhydride is trifluoroacetic anhydride. Suitable solvents include methylene chloride, chloroform as well as ethers, including tetrahydrofuran, diethyl ether and 1,4-dioxane. The preferred solvent is methylene chloride. Suitable bases include triethylamine, pyridine, and sodium hydrogen carbonate. The preferred base is pyridine. The reaction is conducted at a temperature of from about 0° C. to about 65° C., preferably at about 25° C.

Compounds of the formula XI can be prepared using methods known to one skilled in the art, such as, for example, as outlined in European Patent Application Pub. No. 0 438 230 A2.

Compounds of formula IX where W is oxygen, X and Z are nitrogen, and Y is carbon can also be prepared by reacting together compounds of the formula

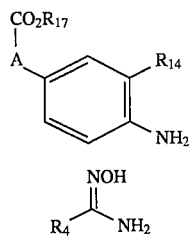   XII

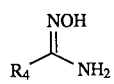   XIII wherein A, $R_4$, $R_{12}$ are as defined above, and $R_{17}$ is $C_1$–$C_8$ alkyl or aryl in an inert solvent in the presence of a base [P. Sauerberg, et al. J. Med. Chem., 687 (1991), G. A. Showell, J. Med. Chem., 1086 (1991) and European Patent Application Pub. No. 0 438 230 A2]. Suitable solvents include ethers such as tetrahydrofuran, 1,4-dioxane, and diethyl ether, methylene chloride, chloroform, carbon tetrachloride, and $C_1$–$C_6$ alcohols. The preferred solvent is tetrahydrofuran. Suitable bases included sodium metal, sodium hydride, potassium hydride, and potassium t-butoxide. The preferred base is sodium hydride. The reaction is conducted at a temperature of about 0° C. to 101° C., preferably at about 66° C.

Compounds of formula XII, if not commercially available, can be prepared via the reaction of a compound of the formula

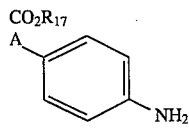   XIV wherein A and $R_{17}$ are as defined above with either chlorine, bromine, or iodine in a suitable solvent with a suitable base. Reaction with bromine is preferred. Suitable solvents include $C_1$–$C_6$ alcohols, methylene chloride, chloroform, or carbon tetrachloride. The preferred solvent is methanol. Suitable bases include triethylamine, pyridine, sodium carbonate, and sodium hydrogen carbonate. The preferred base is sodium hydrogen carbonate. The reaction is conducted at a temperature of about 0° C. to about 65° C., most preferably at about 25° C.

Compounds of the formula XIII can be prepared using methods known to one skilled in the art, such as, for example, C. L. Bell, et al. J. Org. Chem., 2873 (1964).

Compounds of formula XIV are available either commercially or using methods known to one skilled in the art, such as, for example, E. Ferber, et al., Chem. Ber., 839 (1939).

The compounds of the formula I which are basic in nature, are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, i.e., where $R_2$ contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium, magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful psychotherapeutics and are potent serotonin (5-HT$_1$) agonists and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators. The active compounds of the invention can be evaluated as anti-migraine agents by testing the extent to which they mimic sumatriptan in contracting the dog isolated saphenous vein strip [P. P. A. Humphrey et al., Br. J. Pharmacol., 94, 1128 (1988)]. This effect can be blocked by methiothepin, a known serotonin antagonist, Sumatriptan is known to be useful in the treatment of migraine and produces a selective increase in carotid vascular resistance in the anesthetized dog. It has been suggested [W. Fenwick et al., Br. J. Pharmacol., 96, 83 (1989)] that this is the basis of its efficacy.

The serotonin 5-HT$_1$ agonist activity can be measured in in vitro receptor binding assays as described for the 5-HT$_{1A}$ receptor using rat cortex as the receptor source and [$^3$H]-8-OH-DPAT as the radioligand [D. Hoyer et al. Eur. J. Pharm., Vol. 118, 13 (1985)] and as described for the 5-HT$_{1D}$ receptor using bovine caudate as the receptor source and [$^3$H]serotonin as the radioligand [R. E. Heuring and S. J.

Peroutka, *J. Neuroscience*, Vol. 7, 894 (1987)] 5-HT$_1$. agonist activity is defined by agents with affinities (IC$_{50}$'s) of 250 nM or less at either binding assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult are preferably arranged so that each metered dose or "puff" of aerosol contains 20 μg to 1000 μg of the compound of the invention. The overall daily does with an aerosol will be within the range 100 μg to 10 mg. Administration may be several times daily, for example 2, 3, 4 or 8 times, giving for example, 1, 2 or 3 doses each time.

The following Examples illustrate the preparation of the compounds of the present invention. Melting points are uncorrected. NMR data are reported in parts per million (d) and are referenced to the deuterium lock signal from the sample solvent. Specific rotations were measured at room temperature using the sodium D line (589 nm). Unless otherwise stated, all mass spectrum were performed using electron impact (EI, 70 eV) conditions.

Commercial reagents were utilized without further purification. Chromatography refers to column chromatography performed using 32–63 μm silica gel and executed under nitrogen pressure (flash chromatography) conditions. Room temperature refers to 20°–25° C.

EXAMPLE 1

General Procedure for the Hydride Reduction of 3-(N-Benzyloxycarbonyl-pyrrolidin-2-ylmethyl)-1H-indoles Forming 3-(N-Methylpyrrolidin-2-ylmethyl)-1H-indoles To a stirred mixture of lithium aluminum hydride (0.152 g, 4.00 mmol, 2 eq.) in anhydrous tetrahydrofuran (10 mL) at 0° C. was added rapidly a solution of the 3-(N-benzyloxycarbonyl-pyrrolidin-1-ylmethyl)-1H-indole (2.00 mmol) in anhydrous tetrahydrofuran (5 mL). The resulting mixture is heated at reflux under a nitrogen atmosphere for 3 hours. The reaction mixture is cooled, and water (0.25 mL), 15% aqueous sodium hydroxide (0.25 mL), and then more water (0.75 mL) were added sequentially. The resulting mixture was stirred at 25° C. for 30 minutes, filtered, and the filtrate was evaporated under reduced pressure. The residue was column chromatographed using silica gel (approximately 50 g) and elution with a solution methylene chloride: methanol: ammonium hydroxide [9:1:0.1] or other appropriate solvent system to afford the corresponding 3-(N-methylpyrrolidin-2-ylmethyl)-1 H-indole.

Following this procedure the following compounds were prepared:

A. (R)-5-(4-benzyl-1,3-thiazol-2-yl)-3-(N-methylpyrrolidin-2-ylmethyl)-1 H-indole (R)-5-(4-Benzyl-1,3-thiazol-2-yl)-3-(N-benzyloxycarbonylpyrrolidin-2-yl-methyl)-1 H-indole was used. Chromatography using 5% triethylamine in ethyl acetate afforded the title compound (71%) as a white solid: top, 146.0°–148.0° C.; $^{13}$C NMR (CDCl$_3$) 67 169.8, 157.1, 139.3, 137.3, 129.2, 128.5, 128.0, 126.4, 125.7, 123.2, 121.2, 117.6, 114.8, 113.2, 111.5, 66.6, 57.5, 40.8, 38.1, 31.4, 29.6, 21.9; LRMS (m/z, relative intensity) 387 (M$^+$, 4), 303 (34), 155 (30), 147 (17), 115 (18), 85 (63), 84 (100), 83 (57); [α]$^{25}$=+68° (CHCl$_3$, c=1.0). Anal. calcd. for C$_{24}$H$_{25}$N$_3$S·¼H$_2$O: C, 73.54; H, 6.56; N, 10.72. Found: C, 73.50; H, 6.53; N, 10.57.

B. (R)-5-(3-benzyl-1,2,4-oxadiazol-5-yl)-3-(N-methylpyrrolidin-2-ylmethyl)-1H-indole (R)-5-(3-Benzyl-1,2,4-oxadiazol-5-yl)-3-(N-benzyloxycarbonylpyrrolidin-2-ylmethyl) -1H-indole was used. Column chromatography as described above afforded the title compound (34%) as a tan solid: $^1$H NMR (CDCl$_3$) δ 8.48 (s, 1H), 8.36 (s, 1H), 7.91 (dd, J=8 and 2 Hz, 1H), 7.43–7.25 (m, 6H), 7.12 (s, 1H), 4.13 (s, 2H), 3.28–(m, 2H), 2.77–2.68 (m, 1H), 2.53 (m, 1H), 2.46 (s, 3H), 2.26 (q, J=8 Hz, 1H), 1.92–1.74 (m, 2H), 1.74–1.54 (m, 2H); HRMS, calculated for C$_{23}$H$_{24}$N$_4$O 372.1945, found 372.1978.

C. (R)-5-(3-benzyl,1,2,4-oxadiazol-5-ylmethyl)-3-(N-methylpyrrolidin-2-ylmethyl)-1H-indole (R)-5-(3-Benzyl-1,2,4-oxadiazol-5-ylmethyl)-3-(N-benzyloxycarbonylpyrrolidin -2-ylmethyl)-1H-indole was used. Column chromatography as described above afforded the title compound (24%) as a beige resin: $^1$H NMR (CDCl$_3$) δ 8.10 (br s, 1H), 7.47 (s, 1H), 7.34–7.18 (m, 6H), 7.08 (dd, J=8 and 2 Hz, 1H), 7.04 (br s, 1H), 4.25 (s, 2H), 4.01 (s, 2H), 3.22–3.07 (m, 2H), 2.66–2.55 (m, 1H), 2.54–2.43 (m, 1H), 2.42 (s, 3H), 2.24 (q, J=8 Hz, 1H), 1.86–1.69 (m, 2H), 1.68–1.50 (m, 2H); HRMS calculated for C$_{24}$H$_{26}$N$_4$O 386.2070, found 386.2074.

EXAMPLE 2

General Procedure for the Catalytic Reduction of 3-(N-Benzyloxycarbonyl-pyrrolidin -2-ylmethyl)-1H-indoles Forming 3-(Pyrrolidin-2-ylmethyl)-1H-indoles A mixture of the 3-(N-benzyloxycarbonylpyrrolidin-2-ylmethyl)-1H-indole (2.00 mmol) and 10% palladium on carbon (0.20 g) in absolute ethanol (15 mL) was shaken under a hydrogen atmosphere (3 atm) for 4–24 hours, depending on substrate. The resulting reaction mixture was filtered through diatomaceous earth, and the filtrate was evaporated under reduced pressure. The residue was column chromatographed using silica gel (approximately 10 g) and elution with a solution of methylene chloride: methanol:ammonium hydroxide [8: 2: 0.2] or other appropriate solvent system to afford the corresponding 3-(pyrrolidin-2-ylmethyl)-1H-indole.

Following this procedure the following compounds were prepared:

A. (R)-5-(4-benzyl-1,3-thiazol-2-yl)-3-(pyrrolidin-2-ylmethyl)-1H-indole (R)-5-(4-Benzyl-1,3-thiazol-2-yl)-3-(N-benzyloxycarbonylpyrrolidin-2-yl-methyl)-1H-indole was used, and the reaction was heated at 40° C. for 24 hours. Chromatography using methylene chloride:methanol:ammonium hydroxide [9:1:0.1] afforded the title compound (12%) as an amorphous solid: $^1$H NMR (CDCl$_3$) δ 9.1 (br s, indole NH), 8.17 (d, J=1.4 Hz, 1H), 7.74 (dd, J=1.6 and 8.5 Hz, 1H), 7.35–7.21 (m, 6H), 7.02 (s, 1H), 6.67 (s, 1H), 4.22 (s, 2H), 3.5 (br s, NH), 3.41–3.29 (m, 1H), 3.03–2.73 (m, 4H), 1.94–1.61 (m, 3H), 1.49–1.38 (m, 1H); $^{13}$C NMR (CDCl$_3$)δ 169.9, 157.0, 139.2, 137.4, 129.2, 128.5, 127.7, 126.4, 125.5, 123.8, 121.2, 117.3, 114.3, 113.3, 111.7, 59.2, 46.0, 38.1, 31.5, 31.1, 24.9; HRMS calculated for C$_{23}$H$_{23}$N$_3$S 374.1615, found 374.1691.

EXAMPLE 3

General Procedure for the Formation of 3-(N-Benzyloxycarbonylpyrrolidin-2-ylmethyl)-1H-indoles Via the Palladium Catalyzed Cyclization of 1-(N-Benzyloxycarbonylpyrrolidin-2-yl)-3-(N-(2-halophenyl)-N-trifluoroacetylamino)-propenes A mixture of the 1-(N-benzyloxycarbonylpyrrolidin-2-yl)-3-(N-(2-halophenyl)-N-trifluoroacetylamino)propene (2.00 mmol), tetrabutylammonium chloride (2.00 mmol), and palladium(II) acetate (0.089 g, 0.40 mmol, 0.2 eq) in a solution of triethylamine (8 mL) and anhydrous N,N-dimethylformamide (4 mL) was heated at reflux under nitrogen for 2 hours. The resulting reaction mixture was evaporated under reduced pressure, and the residue was partitioned between ethyl acetate (25 mL) and water (25 mL). The ethyl acetate layer was removed, and the aqueous layer was extracted with ethyl acetate (25 mL). The organic extracts were combined, dried (M$_g$SO$_4$), and evaporated under reduced pressure. The residue was column chromatographed using silica gel (approximately 50 g) and elution with 40% ethyl acetate in hexanes or an appropriate solvent system to afford the corresponding 3-(N-benzyloxycarbonylpyrrolidin-2-ylmethyl)-1 H-indole.

Following this procedure the following compounds were prepared:

A. (R)-5-(4-Benzyl-1,3-thiazol-2-yl)-3-(N-benzyloxycarbonylpyrrolidin-2-yl-methyl)-1H indole (R)-1-(N-Benzyloxycarbonylpyrrolidin-2-yl)-3-(N-(2-bromo-4-(4-benzyl-1,3-thiazol-2-yl)phenyl)-N-trifluoroacetylamino)propene was used. Chromatography using elution with ethyl acetate gradient in hexanes [1:3 to 2:5] afforded the title compound (58%) as a pale yellow foam: FAB LRMS (m/z, relative intensity) 509 (MH$^+$, 37), 508(M$^+$, 100), 462 (5), 372 (8), 304 (33); FAB HRMS calculated for [C$_{31}$H$_{30}$N$_3$O$_2$S·H]$^+$509.2139, found 509.2106. Anal. calcd for C$_{31}$H$_{30}$N$_3$O$_2$S·½ C$_4$H$_8$O$_2$ [ethyl acetate]: C, 71.71; H, 6.20; N, 7.60. Found: C, 71.55: H, 5.82; N, 7.64.

B. (R)-5-(3-Benzyl-1,2,4-oxadiazol-5-yl)-3-(N-benzyloxycarbonylpyrrolidin-2-ylmethyl)-1H-indole (R)-1 -(N-Benzyloxycarbonylpyrrolidin-2-yl)-3-(N-(2-bromo-4-(3-benzyl-1,2,4-oxadiazol-5-yl)phenyl)-N-trifluoroacetylamino)propene was used. Column chromatography using the above described solvent system afforded the title compound (74%) as a light yellow resin: R$_1$=0.41 (hexane-EtOAc 50:50); HRMS calculated for C$_{30}$H$_{29}$N$_4$O$_3$ 493.2288, found: 493.2240.

C. (R)-5-(3-Benzyl-1,2,4,-oxadiazol-5-ylmethyl)-3-(N-benzyloxycarbonylpyrrolidin -2-yl-methyl)-1H-indole (R )-1-(N-Benzyloxycarbonylpyrrolidin-2-yl)-3-(N-(2-bromo-4-(3-benzyl-1,2,4-oxadiazol-5-ylmethyl)phenyl)-N-trifluoroacetylamino)propene was used. Column chromatography using the above described solvent system afforded the title compound (61%) as a tan resin: R$_1$=0.063 (hexane-EtOAc 50:50); HRMS calculated for C$_{31}$H$_{31}$N$_4$O$_3$ 507.2396, found: 507.2387.

EXAMPLE 4

General Procedure for the Formation 1-(N-Benzyloxycarbonylpyrrolidin-2-yl)-3-(N-2-halophenyl)-N-trifluoroacetylamino)propenes from the Mitsunobu Coupling of 2-Halo -N-trifluoroacetylanilines with 1-(N-Benzyloxycarbonylpyrrolidin-2-yl)-3-hydroxypropene To a stirred solution of 1-(N-benzyloxycarbonylpyrrolidin-2-yl)-3-hydroxypropene (R, or S, or racemate, 2.00 mmol), the 2-halo-N-trifluoroacetylaniline (2.5 mmol, 1.25 eq), and triphenylphosphine (0.655 g, 2.50 mmol, 1.25 eq) in anhydrous tetrahydrofuran (15 mL) at 0° C. under a nitrogen atmosphere was added diethyl azodicarboxylate (0.39 mL, 2.48 mmol, 1.25 eq) dropwise. The reaction solution was slowly warmed to 25° C. over the course of 2 hours, and then stirred at 25° C. under a nitrogen atmosphere for an additional 12 hours. The resulting reaction solution was evaporated under reduced pressure, and the residue was column chromatographed using silica gel (approximately 150 g) and elution with an appropriate solvent system to afford the corresponding 1-(N-benzyloxycarbonylpyrrolidin-2-yl)-3-(N-(2-halophenyl)-N-trifluoroacetyl-amino)propene.

Following this procedure the following compounds were prepared:

A. (R)-1-(N-Benzyloxycarbonylpyrrolidin-2-yl)-3-(N-(2-bromo-4-(4-benzyl-1,3-thiazol-2-yl)phenyl)-N-trifluoroacetylamino)propene 4-(4-Benzyl-1,3-thiazol-2-yl)-2-bromo-1-trifluoroacetylaminobenzene and (R)-1-(N-benzyloxycarbonylpyrrolidin-2-yl)-3-hydroxypropene were used. Chromatography using elution with a 1–5% either gradient in methylene chloride afforded the title compound (97%) as a white foam: FAB LRMS (m/z, relative intensity) 686 ($MH_2^+$, 100), 685 ($MH^+$, 60), 684 ($M^+$, 90), 640 (23), 578 (15), 441 (17), 371 (20); FAB HRMS calculated for $[C_{33}H_{29}BrF_3N_3O_3S \cdot H]^+$ [with $^{78}Br$ and $^{32}S$] 664.1145, found 684.1157.

B. (R)-1-(N-Benzyloxycarbonylpyrrolidin-2-yl)-3-(N-(2-bromo-4-(3-benzyl-1,2,4-oxadiazol-5-yl)phenyl)-N-trifluoroacetylamino)propene 4-(3-Benzyl-1,2,4-oxadiazol-5-yl)-2-bromo-1-trifluoroacetylaminobenzene and (R)-1-(N-benzyloxycarbonylpyrrolidin-2-yl)-3-hydroxypropene were used. Chromatography using elution with 5% either in methylene chloride afforded the title compound (88%) as a thick yellow oil: $R_f$=0.32 ($CHCl_3$); LRMS (m/z, relative intensity) 669 (M+, 25).

C. (R)-1(N-Benzyloxycarbonylpyrrolidin-2-yl)-3-(N-(2-bromo-4-(3-benzyl-1,2,4-oxadiazol-5-ylmethyl)phenyl)-N-trifluoroacetylamino)propene 4-(3-Benzyl-1,2,4-oxadiazol-5-ylmethyl)-2-bromo-1-trifluoroacetylaminobenzene and (R)-1-(N-benzyloxycarbonylpyrrolidin-2-yl)-3-hydroxypropene were used. Chromatography using elution with 5% either in methylene chloride afforded the title compound (90%) as a thick yellow oil: $R_f$=0.75 ($CHCl_3$—$CH_3OH$ 20:1); LRMS (m/z, relative intensity) 683 (M+,18).

EXAMPLE 5

(R)-1-(N-Benzyloxycarbonylpyrrolidin-2-yl)-3-hydroxypropene

To a stirred solution of ethyl (R)-3-(N-benzyloxycarbonylpyrrolidin-2-yl)-2-propenoate (3.03 g, 10.00 mmol) in anhydrous tetrahydrofuran (75 mL) at −78° C. under nitrogen was added dropwise a solution of diisobutylaluminum hydride (1.0M in hexanes, 22.0 mL, 22.0 mmol, 2.2 eq). The resulting solution was stirred at −78° C. under nitrogen for 30 minutes. The reaction solution was then allowed to warmed to room temperature over the course of 2 hours. A saturated solution of sodium hydrogen carbonate (50 mL) was added, and the aqueous mixture was extracted with ethyl acetate (3×50 mL). The extracts were combined, dried ($MgSO_4$), and evaporated under reduced pressure. Column chromatography of the residue with an diethyl ether/hexanes [1:1] afforded the title compound as a clear colorless oil (1.41 g, 5.40 mmol, 54%): $^1H$ NMR ($CDCl_3$) δ 7.40–7.25 (m, 5H), 5.75–5.53 (m, 2H), 5.20–5.00 (m, 2H), 4.38 (br m, 1H), 4.06 (br d, J=13.7 Hz, 3H), 3.45 (br t, J=7.0 Hz, 1H), 2.03–1.68 (m, 4H); $[a]^{25}$=+34° (MeOH, c=1.0); HRMS calculated for $C_{15}H_{19}NO_3$ 261.1365, found 261.1356.

EXAMPLE 6

Ethyl (R)-3-(N-Benzyloxycarbonylpyrrolidin-2-yl)-2-propenoate

To a stirred solution of N-carbobenzyloxypyrrolidine-2-carboxaldehyde (1.17 g, 5.00 mmol) in anhydrous tetrahydrofuran at −78° C. was added (carboethoxymethylene)triphenylphosphorane (2.09 g, 6.00 mmol. 1.2 eq) as a solid portionwise. The resulting reaction mixture was stirred at room temperature under nitrogen for 2 hours, and then heated at reflux under nitrogen for 1 hour. The reaction mixture was evaporated under reduced pressure and the residue was column chromatographed using silica gel (approximately 100 g) and elution with 20% diethyl ether in hexanes to afford the title compound as a clear, colorless oil (1.11 g, 3.65 mmol, 73%): $^1H$ NMR ($CDCl_3$) δ 7.34–7.25 (m, 5H), 6.89–6.76 (m, 1H), 5.88–5.74 (m, 1H), 5.18–5.05 (m, 2H), 4.60–4.43 (m, 1H), 4.17 (q, J=7.1 Hz, 2H), 3.55–3.40 (m, 2H), 2.11–2.00 (m, 1H), 1.90–1.75 (m, 3H), 1.28 (t, J=7.1 Hz, 3H); $^{13}C$ NMR ($CDCl_3$) [Note: due to slow nitrogen inversion two conformers of the products are seen by NMR spectroscopy] δ 166.3, 154.7, 147.9, 147.4, 136.6, 128.4, 127.9, 120.9, 66.9, 65.8, 60.4, 58.1, 57.7, 46.8, 46.4, 31,6, 30.8, 23.6, 22.8, 22.6, 15.3, 14.2.

EXAMPLE 7

General Synthesis of 2-Halo-N-trifluoroacetylanilines from Reaction of 2-Haloanilines and Trifluoroacetic Anhydride To a stirred solution of the 2-haloaniline (2.00 mmol) and pyridine (0.18 mL, 2.22 mmol, 1.1 eq) in anhydrous methylene chloride (10 mL) at 0° C. under a nitrogen atmosphere was added dropwise trifluoroacetic anhydride (0.31 mL, 2.19 mmol, 1.1 eq). The resultant reaction mixture was stirred at 0° C. under a nitrogen atmosphere for 3 hours. A saturated solution of sodium hydrogen carbonate was added (15 mL), and this aqueous mixture was extracted with ethyl acetate (3×15 mL). The extracts were combined, dried ($MgSO_4$), and evaporated under reduced pressure. If necessary, the residue was column chromatographed using silica gel (approximately 50 g) and elution with an ethyl acetate gradient in hexanes to afford the corresponding 2-halo-N-trifluoroacetylaniline.

Following this procedure the following compounds were prepared:

A. 4-(4-Benzyl-1,3-thiazol-1-yl)-2-bromo-1-trifluoroacetylaminobenzene 4-(4-Benzyl-1,3-thiazol-2-yl)-2-bromoaniline was used. The extraction residue was triturated in diethyl ether/hexanes [1:1, 10 mL] to afford the title compound (92%) as a white powder: top, 102.0°–104.0° C.; $^{13}$C NMR (CDCl$_3$) δ 164.9, 158.0, 138.7, 134.1, 132.6, 130.1, 129.1, 128.6, 126.8, 126.6, 121.8, 115.2, 114.4, 38.0. Anal. calcd for $C_{18}H_{12}F_3BrN_2OS$: C, 48.99; H, 2.74; N, 6.35. Found: 48.72; H, 2.58; N, 6.29.

B. 4-(3-Benzyl-1,2,4-oxadiazol-5-yl)-2-bromo-1-trifluoroacetylaminobenzene 4-(3-Benzyl-1,2,4-oxadiazol-5-yl)-2-bromoaniline was used. Column chromatography as described above afforded the title compound (81%) as a white solid: mp, 152.0°–153.0° C.; $^1$H NMR (CDCl$_3$) δ 8.64 (br s, 1H), 8.53 (d, J=8 Hz, 1H), 8.83 (d, J=2 Hz, 1H), 8.13 (dd, J=8 and 2 Hz, 1H), 7.40–7.26 (m, 5H), 4.14 (s, 2H); LRMS (m/z, relative intensity) 426 (M+,85).

C. 4-(3-Benzyl-1,2,4-oxadiazol-5-ylmethyl)-2-bromo-1-trifluoroacetylaminobenzene 4-(3-Benzyl-1,2,4-oxadiazol-5-ylmethyl)-2-bromoaniline was used. Column chromatography as described above afforded the title compound (90%) as a yellow resin: $^1$H NMR (CDCl$_3$) δ 8.59 (br s, 1H); 8.36 (br s, 1H), 8.22 (d, J=8 Hz, 1H), 7.42 (s, 1H), 7.24–7.32 (m, 5H), 4.10 (s, 2H), 4.01 (s, 2H); LRMS (m/z, relative intensity) 440 (M+,90).

EXAMPLE 8

4-(4-Benzyl-1,3-thiazol-2-yl)-2-bromoaniline

A mixture of 4-amino-3-bromobenzthioamide (1.66 g, 7.18 mmol) and 1-chloro-3-phenylacetone [Tarhouni, R. et al., *Tetrahedron Letters*, 835 (1964)] (1.36 g, 8.07 mmol, 1.1 eq) in absolute ethanol (18 mL) was heated at reflux under nitrogen for 2.5 hours. The resulting reaction mixture was evaporated under reduced pressure, and the residue was partitioned between ethyl acetate (20 mL) and a saturated solution of sodium hydrogen carbonate (20 mL). The ethyl acetate layer was removed, and the aqueous layer was extracted with ethyl acetate (2×20 mL). The organic extracts were combined, dried (MgSO$_4$), and evaporated under reduced pressure. The residual solid was chromatographed using silica gel (approximately 175 g) and elution with an ethyl acetate gradient in hexanes [1:4 to 1:1] to afford the title compound (68%) as a pale yellow solid: top, 110°–115° C.; $^{13}$C NMR (CDCl$_3$) δ 166.8, 157.1, 145.6, 139.1, 130.7, 129.1, 128.6, 126.9, 126.4, 125.4, 115.3, 113.2, 109.2, 38.0. Anal. calcd for $C_{16}H_{13}BrN_2S$: C, 55.66; H, 3.79; N, 8.11. Found: C, 55.36; H, 3.71; N, 7.92.

EXAMPLE 9

4-Amino-3-Bromobenzthioamide

A stirred solution of 4-amino-3-bromobenzonitrile (6.92 g, 35.1 mmol) and diethyl dithiophosphate (17.7 mL, 105 mmol, 3 eq.) in absolute ethanol (160 mL) at 0° C. was perfused with hydrogen chloride gas at a moderate rate for 30 minutes. The resulting reaction mixture was stirred at room temperature for 12 hours, and then solvent was removed via evaporation under reduced pressure. The residue was suspended in a saturated solution of sodium hydrogen carbonate (25 mL), and this aqueous mixture was extracted with ethyl acetate (3×25 mL). The organic extracts were combined, dried (MgSO$_4$), and evaporated under reduced pressure. The residue was chromatographed using silica gel (approximately 300 g) and elution with an acetone gradient in methylene chloride [1:50 to 1:20] to afford the title compound (1.02 g, 25%) as an amorphous yellow solid: $^1$H NMR (DMSO-d$_6$) δ 9.41 (br s, NH), 9.13 (br s, NH), 9.13 (br s, NH), 8.11 (d, J=2.1 Hz, 1H), 7.78 (dd, J=2.1 and 8.6 Hz, 1H), 6.72 (d, J=8.7 Hz, 1H), 6.03 (s, 2NH); TLC: RB$_1$=0.15[1% diethyl ether in methylene chloride].

EXAMPLE 10

General Procedure for the Formation of 2-Halo-4-(1,2,4-oxadiazol-5-yl)anilines or 2-Halo-4-(1,2,4-oxadiazol-5-ylmethyl)anilines from the Condensation of the Corresponding Alkyl 4-Amino-3-halobenzoates or Alkyl 2-(4-Amino-3-halophenyl)acetates, respectively, with Phenylacetamide Oxime Sodium hydride (87 mg of an 60% oil dispersion, 2 mmol) was added to a stirred solution of phenylacetamide oxime (0.33 g, 2.2 mmol, 1.1 eq) [C. L. Bell, et al., *J. Org. Chem.*, 2873 (1964)] in anhydrous THF (10 ml), and the resulting reaction mixture was heated at reflux for 30 minutes. A solution of the alkyl 4-amino-3-halobenzoate or alkyl 2-(4-amino-3-halophenyl)acetate (1 mmol) in anhydrous THF (5 mL) was then added, and the reaction was heated under reflux for 2 hours. The mixture was allowed to cool to room temperature before water (10 ml) was added. The resulting aqueous mixture was extracted with dichloromethane (3×25 ml). The extracts were combined, dried (MgSO$_4$), and evaporated under reduced pressure. The residue was chromatographed using silica gel (20 g) and elution with chloroform to afford the corresponding 2-halo-4-(1,2,4-oxadiazol-5-yl)aniline or 2-halo-4-(1,2,4-oxadiazol-5-ylmethyl)aniline, respectively.

Following this procedure the following compounds were prepared:

A. 4-(3-Benzyl-1,2,4-Oxadiazol-5-yl)-2-bromoaniline

Methyl 4-amino-3-bromobenzoate was used. Column chromatography as described above afforded the title compound (33%) as a tan solid; mp 144°–145° C.; $^1$H NMR (CDCl$_3$) δ 8.18 (d, J=2 Hz, 1H), 7.82 (dd, J=8 and 2 Hz, 1H), 7.39–7.25 (m, 5H), 6.77 (d, J=8 Hz, 1H), 4.09 (s, 2H); LRMS (m/z, relative intensity) 330 (M+,90).

B. 4-(3-Benzyl-1,2,4-oxadiazol-5-ylmethyl)-2-bromoaniline

Ethyl 2-(4-amino-3-bromophenyl)acetate was used. Column chromatography as described above afforded the title compound (41%) as a yellow resin; $^1$H NMR (CDCl$_3$) δ 7.34–7.24 (m, 6H), 7.00 (dd, J=8 and 2 Hz, 1H), 6.69 (d, J=8 Hz, 1H), 4.02 (s, 2H), 4.01 (s, 2H); LRMS (m/z, relative intensity) 334 (M+,15).

EXAMPLE 11

General Procedure for the Bromination of Anilines to Form 2-Bromoanilines

To a stirred mixture of the aniline (2.00 mmol) and sodium hydrogen carbonate (0.21 g, 2.50 mmol, 1.25 eq) in methanol (10 mL) at 0° C. was added dropwise bromine (0.113 mL, 2.19 mmol, 1.1 eq). The resulting reaction mixture was then stirred at 25° C. for 30 minutes. The reaction mixture was then evaporated under reduced pressure, and the residue was placed in a saturated solution of sodium hydrogen carbonate (10 mL). This aqueous mixture was extracted with ethyl acetate (3×15 mL). The extracts were combined, dried (MgSO$_4$), and evaporated under reduced pressure. The residue was column chromatographed using silica gel (approximately 50 g) and elution with an appropriate solvent system to afford the corresponding 2-bromoaniline.

Following this procedure the following compounds were prepared:

A. 4-Amino-3-bromobenzonitrile

4-Aminobenzonitrile was used. Chromatography using elution with a gradient of ethyl acetate in hexanes [1:5 to 1:3] afforded the title compound (71%) as a white solid: $^1$H NMR (CDCl$_3$) δ 7.65 (d, J=2.1 Hz, 1H), 7.34 (dd, J=2.1 and 8.1 Hz, 1H), 6.71 (d, J=8.0 Hz, 1H), 4.6(br s, 2NH); TLC:R$_1$=0.25 [ethyl acetate/hexanes, 1:3].

B. Methyl 4-amino-3-bromobenzoate

Methyl 4-aminobenzoate was used. Chromatography using elution with ethyl acetate in hexanes [1:4] afforded the title compound (36%) as an orange oil: $^1$H NMR (CDCl$_3$) δ 8.09 (d, J=2 Hz, 1H), 7.75 (dd, J=9 and 2 Hz, 1H), 6.71 (d, J=9 Hz, 1H), 4.49 (br s, 2H), 3.84 (s, 3H); HRMS (m/z, relative intensity) 230 (M+,100).

C. Ethyl 2-(4-amino-3-bromophenyl)acetate

Ethyl 2-(4-aminophenyl)acetate was used. Chromatography using elution with ethyl acetate in hexanes [1:4] afforded the title compound (25%) as a light brown oil: $^1$H NMR (CDCl$_3$) δ 7.33 (d, J=2 Hz, 1H), 7.02 (dd, J=8 and 2 Hz, 1H), 6.76 (dd, J=8Hz, 1H), 4.11 (q, J=7 Hz, 2H), 3.45 (s, 2H), 1.23 (t, J=7 Hz, 3H); LRMS (m/z, relative intensity) 258 (M +,100).

We claim:

1. A compound of the formula where A represents a direct bond, C$_1$–C$_4$ alkylene, or C$_1$–C$_4$ alkenylene; n is 0, 1, or 2; R$_1$ is hydrogen, C$_1$–C$_6$ alkyl, aryl, C$_1$–C$_3$ alkylaryl, C$_1$–C$_3$ alkylheteroaryl, or —(CH$_2$)$_m$R$_6$; W, X, Y, and Z are each independently oxygen, sulfur, nitrogen or carbon, provided that at least one of W, X, Y or Z is nitrogen; R$_2$, R$_3$, R$_4$, and R$_5$ are each independently hydrogen, C$_1$–C$_6$ alkyl, aryl, C$_1$–C$_3$ alkylaryl, C$_1$–C$_3$ alkylheteroaryl, halogen, cyano, trifluoromethyl, nitro, —OR$_7$, —NR$_7$R$_8$, —(CH$_2$)$_s$OR$_7$, —SR$_7$, —SO$_2$NR$_7$R$_8$, —NR$_7$SO$_2$R$_8$, —NR$_7$CO$_2$R$_8$, —CONR$_7$R$_8$, or —CO$_2$R$_7$; one of R$_2$ and R$_3$, R$_3$ and R$_4$, or R$_4$ and R$_5$ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; R$_6$ is cyano, trifluoromethyl, or —OR$_9$; R$_7$, R$_8$, and R$_9$ are each independently hydrogen, C$_1$ to C$_6$ alkyl, —(CH$_2$)$_m$R$_{10}$, C$_1$ to C$_3$ alkylaryl, or aryl; R$_7$ and R$_8$ may be taken together to form a C$_4$–C$_7$ alkyl ring; R$_{10}$ is cyano, trifluoromethyl, or C$_1$–C$_4$ alkoxy; R$_{11}$ is hydrogen, —OR$_{12}$, or —NCHOR$_{12}$; R$_{12}$ is C$_1$ to C$_6$ alkyl, aryl, or C$_1$ to C$_3$ alkyl-aryl; m is 1, 2, or 3; s is 0, 1, 2, or 3; and the above aryl groups and the aryl moieties of the above alkylaryl groups are independently selected from phenyl and substituted phenyl, wherein said substituted phenyl may be substituted with one to three groups selected from C$_1$ to C$_4$ alkyl, halogen, hydroxy, cyano, carboxamido, nitro, and C$_1$ to C$_4$ alkoxy, and the pharmaceutically acceptable salts thereof.

2. A compound according to claim 1, wherein the compound of Formula I is

3. A compound according to claim 2, wherein the compound is the cis epimer.

4. A compound according to claim 1 wherein A is a direct bond or —CH$_2$—; n is 1; R$_1$ is hydrogen, C$_1$–C$_4$ alkyl, or —CH$_2$CH$_2$OCH$_3$; Z is nitrogen; Y is carbon; W and X are each independently oxygen, sulfur, nitrogen or carbon; R$_{11}$ is hydrogen or —OCH$_3$.

5. A compound according to claim 4, wherein the compound of Formula I is

6. A compound according to claim 5, wherein the compound is the cis epimer.

7. A compound according to claim 1, said compound being selected from (R)-5-(4-benzyl-1,3-thiazol-2-yl)-3-(N-methylpyrrolidin-2-ylmethyl)-1H-indole;

(R)-5-(4-benzyl-1,3-thiazol-2-yl)-3-(pyrrolidin-2-ylmethyl)-1H-indole;

(R)-5-(3-benzyl-1,2,4-oxadiazol-5-yl)-3-(N-methylpyrrolidin-2-ylmethyl)-1H-indole;

(R)-5-(3-benzyl-1,2,4-oxadiazol-5-yl)-3-(pyrrolidin-2-ylmethyl)-1H-indole;

(R)-5-(3-benzyl-1,2,4-oxadiazol-5-ylmethyl)-3-(N-methylpyrrolidin-2-ylmethyl)-1H-indole; and (R)-5-(3-benzyl-1,2,4-oxadiazol-5-ylmethyl)-3-(pyrrolidin-2-ylmethyl)-1H-indole.

8. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

9. A pharmaceutical composition for treating disorders arising from deficient serotonergic neurotransmission comprising an amount of a compound according to claim 1 effective in treating such a disorder and a pharmaceutically acceptable carrier.

10. A method of treating a condition selected from hypertension, depression, anxiety, eating disorders, obesity, drug abuse, cluster headache, migraine, pain, and chronic paroxysmal hemicrania and headache associated with vascular disorders comprising administering to a mammal requiring such treatment an amount of a compound according to claim 1 effective in treating such condition.

11. A method for treating disorders arising from deficient serotonergic neurotransmission comprising administering to a mammal requiring such treatment an amount of a compound according to claim 1 effective in treating such condition.

12. A compound of the formula

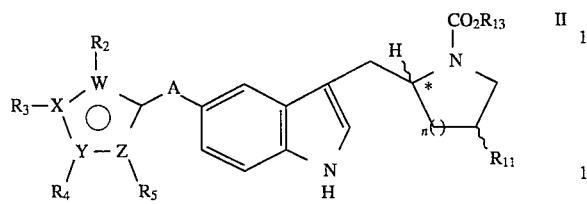

where A represents a direct bond, $C_1$–$C_4$ alkyl, or $C_1$–$C_4$ alkenyl; n is 0, 1, or 2; W, X, Y, and Z are each independently oxygen, sulfur, nitrogen or carbon, provided that at least one of W, X, Y or Z is nitrogen; $R_2$, $R_3$, $R_4$, and $R_5$ are each independently hydrogen, $C_1$–$C_6$ alkyl, aryl, $C_1$–$C_3$ alkylaryl, $C_1$–$C_3$ alkylheteroaryl, halogen, cyano, trifluoromethyl, nitro, —$O_7$, —$NR_7R_8$, —$(CH_2)_sOR_7$, —$SR_7$, —$SO_2NR_7R_8$, —$NR_7SO_2R_8$, —$NR_7CO_2R_8$, —$CONR_7R_8$, or —$CO_2R_7$; one of $R_2$ and $R_3$, $R_3$ and $R_4$, or $R4$ and $R_5$ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; $R_7$ and $R_8$ are each independently hydrogen, $C_1$ to $C_6$ alkyl, —$(CH_2)_mR_{10}$, $C_1$ to $C_3$ alkylaryl, or aryl; $R_7$ and $R_8$ may be taken together to form a $C_4$–$C_7$ alkyl ring; $R_{10}$ is cyano, trifluoromethyl, or $C_1$–$C_4$ alkoxy; m is 1, 2, or 3; s is 0, 1, 2, or 3; $R_{11}$ is hydrogen, —$OR_{12}$, or —NHCOR$_{12}$; $R_{12}$ is $C_1$ to $C_6$ alkyl, aryl, or $C_1$ to $C_3$ alkyl-aryl; $R_{13}$ is $C_1$–$C_6$ alkyl, aryl, or alkylaryl; and the above aryl groups and the aryl moieties of the above alkylaryl groups are independently selected from phenyl and substituted phenyl wherein said substituted phenyl may be substituted with one to three groups selected from $C_1$ to $C_4$ alkyl, halogen, hydroxy, cyano, carboxamido, nitro, and $C_1$ to $C_4$ alkoxy.

13. A compound according to claim 12, wherein the compound of formula II is

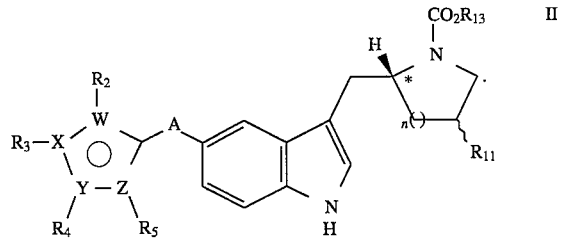

14. A compound according to claim 13, wherein the compound is the cis epimer.

15. The compound of claim 12, wherein A is a direct bond or —$CH_2$—; n is 1, Z is nitrogen; Y is carbon; W and X are each independently oxygen, sulfur, nitrogen or carbon; $R_{11}$ is hydrogen or —$OCH_3$.

16. A compound according to claim 15, wherein the compound of formula II is

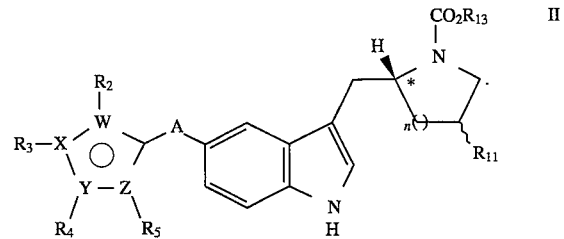

17. A compound according to claim 16, wherein the compound is the cis epimer.

* * * * *